United States Patent [19]

Saitoh et al.

[11] Patent Number: 4,923,893

[45] Date of Patent: May 8, 1990

[54] EXTERNAL PREPARATION OF VITAMIN-E

[75] Inventors: Izumi Saitoh, Hyogo; Shigeru Kido; Yoshio Doi, both of Osaka; Shohei Egawa, Hyogo, all of Japan

[73] Assignee: Shionogi & Co., Ltd., Osaka, Japan

[21] Appl. No.: 267,284

[22] Filed: Nov. 4, 1988

[30] Foreign Application Priority Data

Dec. 8, 1987 [JP] Japan .................. 62-310481

[51] Int. Cl.$^5$ ................. A61K 31/355; A61K 31/185
[52] U.S. Cl. .................... 514/458; 514/887; 514/577
[58] Field of Search ............... 514/458, 577, 953, 887

[56] References Cited

U.S. PATENT DOCUMENTS 3,627,871  12/1971  Groves et al. .................. 427/78
4,686,211   8/1987  Hara et al. ..................... 514/148

FOREIGN PATENT DOCUMENTS 0265228   4/1988  European Pat. Off. .
63-104909  5/1988  Japan .
63-108013  5/1988  Japan .

Primary Examiner—Douglas W. Robinson
Assistant Examiner—Raymond J. Henley, III
Attorney, Agent, or Firm—Wenderoth, Lind & Ponack

[57] ABSTRACT

External preparations consisting essentially of about 0.1% to about 5% of tocopherol acetate and/or about 0.05% to about 0.3% of glycyrrhetinic acid, about 1% to about 15% of a methacrylic acid-ethyl acrylate copolymer, and about 0.2% to about 3% of a thickening agent in an alcoholic solvent, wherein said copolymer is characterized by that the monomer ratio of ethyl acrylate to methacrylic acid is within a range from 75/25 to 95/5, with residual monomer being 50 ppm or less and with practically no surfactants.

6 Claims, No Drawings

EXTERNAL PREPARATION OF VITAMIN-E

BACKGROUND OF THE INVENTION

1. Field of Invention

This invention relates to preparations of vitamin-E for external use, which are designed for protection of the skin.

2. Prior Art

Hitherto there have been sold in the market many kinds of creams or lotions, whose recommended uses are the prevention of rough skin of the hand, chapping, cracks, frostbite, and the like, and are intended for housewives. It has generally been believed, however, that the rough skin, chapping, cracks in the skin, etc., cannot be prevented unless they would stop doing kitchen work. The reason is that, in most cases, the base ingredients used in conventional creams and lotions are oils and, therefore, these preparations are capable of repelling water for a little while after application, but easily come off, and this fact causes shortened protective action to the skin. Furthermore, this causes oil or odor on tablewares. Therefore, such preparations have been applied after meals or kitchen work, i.e., mainly at bedtime. Consequently, it has been difficult to obtain sufficient skin-protective effect.

SUMMARY OF THE INVENTION

The present invention provides preparations for external use, consisting essentially of about 0.1% to about 5% of tocopherol acetate (hereinafter referred to as vitamin-E or simply as VE) and/or about 0.05% to about 0.3% of glycyrrhetinic acid, about 1% to about 15% of a methacrylic acid-ethyl acrylate copolymer, and about 0.2% to about 3% of a thickening agent in an alcoholic solvent. Percentages or ratios used in this invention mean those by weight (W/W).

DESCRIPTION OF THE PREFERRED EMBODIMENTS

Problem to be Solved

In view of the problems above, the present inventors tried to develop such as VE preparation as to satisfy the undermentioned requirements:

a. Not to give uncomfortable feeling when applied. In other words, to be capable of forming a flexible, thin, and very soft film.

b. To form a strange film. In other words, to form such a film as to resist wash-out with water or neutral detergents for a long period of time and as to resist peel-off.

c. Not to be irritative.

Means to Solve the Problems

The present invention can be achieved by dissolving, in an alcoholic solvent, about 0.1-about 5% of VE, about 0.05-about 0.3% of glycyrrhetinic acid (GRA), about 0.2-about 3% of a cellulose derivative, and about 1-about 15% of a copolymer of methacrylic acid and ethyl acrylate (MAA-EA).

The tocopherol acetate used in this invention is also known as vitamin-E, which has a vasodilating action. Based on this action, it is expected that VE would be effective for acceleration healing of damaged skin, through improving blood circulation of flexibility of capillary vessels.

In addition, GRA is expected to relieve inflammation at the damaged part of the skin and also to prevent the skin from inflammation because of its anti-inflammatory action. In this invention, other pharmaceutically active ingredients such as various vitamins or allantoin may be further contained.

MAA-EA means an acrylic copolymer in which the monomer ratio of ethyl acrylate to methacrylic acid is within a range from 75/25 to 95/5, with residual monomer being 50 ppm or less and with practically no surfactants. The processes for preparing said copolymer are disclosed in JPN Pat. Appln. Nos. 61-253071 and 61-253072, the equivalent of which is EP 265228-A.

The alcoholic solvent in this invention means a lower alkanol including ethanol, propanol, isopropanol, and the like. The alcohol may contain water, but it is preferable to use an alcohol whose alcohol content is 60% or more. Alcohols whose alcohol contents are below this amount are not preferable for this invention, in consideration of the solubility of a thickening agent thereto.

Cellulose derivatives such as ethyl cellulose (EC), hydroxypropyl cellulose (HPC), hydroxypropylmethyl cellulose (HPMC), and the like are preferably used as a thickening agent. Plasticizers, e.g., propylene glycol and the like may be further added.

VE external preparations of the present invention form a film which gives no strange feeling, when applied to the hands, and additionally, the active ingredients therein act on the skin for a long period of time. The film formed on the skin does not come off during kitchen work, etc., and besides, it never results in odor or oils of the preparation on the metals or kitchenwares. Conventional creams and lotions have to be applied very often because active ingredients therein are washed out whenever kitchen work might be done. Moreover, they should be washed out before kitchen work or knitting so that odor or oils do not adhere to articles. Thus, in case of the conventional preparations, the period while active ingredients are acting on the skin is very short in spite of the frequent applications, and this has made it difficult to cure rough skin of the hands, cracks in the skin, and frostbite.

The protective film formed by the preparation of this invention shows a strong resistance to water, neutral detergents, various oils, and the like without preventing the skin from breathing. The preparations are very economical since the drug effectiveness lasts long with their application once to several times a day. Besides, they are easy to handle, since the film formed can be easily and completely washed off with soap or alcohol.

This invention is explained in more detail by the following Examples and Experiments, which are not intended to limit the scope of this invention.

Reference Example (Preparation of Copolymer)

In a closed type reaction vessel with a stirrer which was purged with nitrogen, 236.1 parts by weight of deionized water was charged, and after adjusting the temperature in the reaction vessel to 80° C., 1.2 parts by weight of ammonium persulfate was added and sequentially the following mixture was added in 8 hours.

EA 85 parts by weight
MAA 15 parts by weight

Stirring was continued for another 8 hours by keeping the temperature in the reaction vessel at 80° C. to complete the reaction. The solid content of the emulsion was 30%, in which EA was contained in an amount of 37 ppm, and MAA was less than 10 ppm according to the analysis of the residual monomer by means of gas chromatography. The mean molecular weight of this copolymer was about 840,000.

EXAMPLE 1

Purified water (28.0 g) was put in a closed type vessel equipped with a stirrer. Emulsion (5.0 g as MAA-EA content) prepared in the Reference Example above and 1.0 g of EC were gradually added thereto and the mixture was stirred until the copolymer was dissolved completely.

Isopropanol (65.3 g) was added to the solution of the copolymer and the mixture was stirred to give a clear solution. In the thus obtained clear solution were dissolved 0.5 g of VE and 0.2 g of GRA with stirring to give a VE external preparation.

EXAMPLES 2–6

In substantially the same manner as in Example 1, the following VE preparations were prepared.

TABLE 1

| Component | Example 2 (%) | 3 (%) | 4 (%) | 5 (%) | 6 (%) |
|---|---|---|---|---|---|
| MAA.EA | 1.0 | 10.0 | 15.0 | 5.0 | 5.0 |
| VE | 0.1 | 1.0 | 1.5 | 0.5 | 0.5 |
| GRA | 0.04 | 0.2 | 0.2 | 0.1 | 0.15 |
| EC | 0.2 | 2.0 | 3.0 | 1.0 | 1.0 |
| Purified water | 28.0 | 28.0 | 28.0 | 28.0 | 28.0 |
| Ethanol | Add to make 100 | | Add to make 100 | | |
| IP | | Add to make 100 | | Add to make 100 | Add to make 100 |

(Remark) IP stands for Isopropanol.

EXPERIMENT 1

Water resistance was studied on each film in the following manner.

(Preparations for Study)

[ Preparation of Example 1 (This Invention: VE content 0.5%)
  Commercially Available Cream (Prior Art: VE content 0.5%) ]

(Method)

1. Purified water (500 ml) is put in a cylindrical vessel (15 cm inside diameter and 15 cm high)
2. Preparation (0.5 g each) which contains VE is applied in the middle of the back of the left hand per male volunteer (n=5) and is so spread evenly and circularly as large as 50 mm in diameter.
3. The left hand is dipped in the vessel described in Item (1) and is rubbed with a finger for 3 minutes to remove the formed film.
4. The water in the vessel (3) is collected, and the VE is extracted therefrom with chloroform.
5. The extract is evaporated in vacuo to give a residue, which is dissolved in tetrahydrofuran. The amount of VE removed from the application area is measured by HPLC.
6. The amount of VE still remaining on the application area is determined from the data in Item (5), from which the remaining rate of VE is calculated.

(Result)

TABLE 2

| | Ratio of remaining VE (%) |
|---|---|
| This Invention | 98.2 ± 2.0 |
| Prior Art | 10.7 ± 4.3 |

From the results above, it has been confirmed that the preparations of this invention are much more excellent than commercially available creams in water-resistant property and in remaining rate of active ingredient after hand-washings.

EXPERIMENT 2

How much active ingredient would come off by the contact with clothing was studied in the following manner.

(Preparations for Study)

[ Preparation of Example 1 (This Invention: VE content 0.5%)
  Commercially Available Cream (Prior Art: VE content 0.5%) ]

(Method)

1. Preparation (0.5 g each) is applied in the middle of the back of the hand and then so spread evenly and circularly as large as 50 mm in diameter.
2. Fifteen minutes after the application, the application area is softly wiped with a piece of cellulose nonwoven fabric.
3. The piece of fabric to which test sample is adhered is subjected to extraction with tetrahydrofuran. The VE is quantitatively measured by HPLC.
4. Based on the amount of the VE in Item (3), the come-off rate of VE is calculated.

(Result)

TABLE 3

| | Come-off Rate of VE (%) |
|---|---|
| This Invention | 2.3 |
| Prior Art | 75.7 |

From the results above, it has been confirmed that the preparations of this invention, when applied, lose much smaller amount of active ingredient by contact with clothing than the commercially available creams.

What is claimed is:

1. An external preparation consisting essentially of about 0.1% to about 5% of tocopherol acetate, with or without about 0.05% to about 0.3% of glycyrrhetinic acid; about 1% to about 15% of a methacrylic acid-ethyl acrylate copolymer, in which the monomer ratio of ethyl acrylate to methacrylic acid is within a range from 75/25 to 95/5 with residual monomer being 50 ppm or less and with substantially no surfactants; and 0.2% to about 3% of a thickening agent in a lower alkanol whose concentration in water is 60% or greater.

2. The external preparation claimed in claim 1, wherein said thickening agent is ethyl cellulose, hydroxypropyl cellulose, or hydroxypropylmethyl cellulose.

3. The external preparation claimed in claim 1, wherein said lower alkanol is ethanol or isopropanol whose concentration in water is 60% or greater.

4. An external preparation consisting essentially of (a) about 0.1% to about 5% of tocopherol acetate, (b) about 0.05% to about 0.3% of glycyrrhetinic acid, (c) about 1% to about 15% of a methacrylic acid-ethyl acrylate copolymer, in which the monomer ratio of ethyl acrylate to methacrylic acid is within a range from 75/25 to 95/5 with residual monomer being 50 ppm or less and with substantially no surfactants, and (d) 0.2% to about 3% of a thickening agent in a lower alkanol whose concentration in water is 60% or greater.

5. The external preparation claimed in claim 4, wherein said thickening agent is ethyl cellulose, hydroxypropyl cellulose, or hydroxypropylmethyl cellulose.

6. The external prepration claimed in claim 4, wherein said lower alkanol is ethanol or isopropanol whose concentration in water is 60% or greater.

* * * * *